United States Patent [19]

Wallace et al.

[11] Patent Number: 5,210,414

[45] Date of Patent: May 11, 1993

[54] DIFFERENTIAL SURFACE COMPOSITION ANALYSIS BY MULTIPLE-VOLTAGE ELECTRON BEAM X-RAY SPECTROSCOPY

[75] Inventors: William E. Wallace; Michael J. Keane, both of Morgantown, W. Va.

[73] Assignee: The United States of America as represented by the Department of Health and Human Services, Washington, D.C.

[21] Appl. No.: 676,693

[22] Filed: Mar. 29, 1991

[51] Int. Cl.$^5$ .................. H01J 37/26; G01N 23/225
[52] U.S. Cl. ...................... 250/307; 250/310
[58] Field of Search .................. 250/307, 310, 397

[56] References Cited

U.S. PATENT DOCUMENTS

| | | | |
|---|---|---|---|
| 3,376,419 | 2/1968 | Schumacher | 250/310 |
| 4,037,101 | 7/1977 | Okumura et al. | 250/310 |
| 4,253,154 | 2/1981 | Russ et al. | 250/310 |
| 4,717,826 | 1/1988 | Silver | 250/310 |
| 4,777,364 | 10/1988 | Sartore | 250/307 |
| 4,857,731 | 8/1989 | Tagata | 250/310 |
| 4,962,516 | 10/1990 | Soezima | 250/307 |

OTHER PUBLICATIONS

Wallace, et al., "Clay Occlusion of Respirable Quartz Particles Detected by Low Voltage Scanning Electron Microscopy—X-Ray Analysis", *Ann. Occup. Hyg.*, vol. 34, No. 2, pp. 195-204 (1990).

*Primary Examiner*—Bruce C. Anderson
*Attorney, Agent, or Firm*—Lowe, Price, LeBlanc & Becker

[57] ABSTRACT

A method of differential surface composition analysis which allows non-destructive compositional analysis with depths below a solid surface is used to analyze respirable dust particles to determine the presence of hazardous components in the surface of the dust particles. A method of incubating respirable particles in a surrogate pulmonary surfactant system used in combination with the differential surface composition analysis allows determination of surface components which survive or are exposed on the respiratory particles after incubation in the surrogate pulmonary surfactant, representing modification of the partical surface upon deposition in the lung.

18 Claims, 3 Drawing Sheets

DIFFERENTIAL SURFACE COMPOSITION ANALYSIS BY MULTIPLE-VOLTAGE ELECTRON BEAM X-RAY SPECTROSCOPY

TECHNICAL FIELD

The present invention relates to methods of identifying the composition of particle surfaces. More particularly, the present invention relates to methods of identifying respirable particles which may be pathogenic in the lung.

BACKGROUND ART

Respirable silica particles are well documented agents for the induction of lung diseases following inhalation. However, epidemiologic studies of respirable silica exposures, especially in mixed dust atmospheres, and pneumoconiosis or pulmonary fibrosis show regional or geological formation-specific variations in the correlation of exposure and disease prevalence.

In the United States and elsewhere the silica content of respirable dusts in occupational settings is usually measured for research or regulatory purposes by infrared spectroscopic or X-ray diffraction analysis on bulk samples of filter collected respirable dusts. This provides a mass percent silica value. Scanning electron microscopy X-ray spectrometry (SEM-XRS) is sometimes used for a particle by particle composition analysis. These methods of analysis typically give comparable data, and all fail to explain the variations in exposure and disease seen, for example, between different mining commodities or geologic formations. These exposure measures do not assay the biologically available active fraction of the silica dust; that is, they do not distinguish finely coated silica particles from bare silica surfaced particles, or account for the persistance or lack of persistance of such occlusions under conditions existing on the surface of the lung airways and air sacks.

Mining and some other dusty workplace atmospheres are monitored for respirable dust and quartz dust for purposes of occupational health protection. Respirable quartz exposure data are also acquired for epidemiological research on the correlation of pulmonary disease prevalence with respirable dust composition and concentration. For these purposes quartz content often is measured on collected dust samples by X-ray diffraction or i.r. spectroscopy. Scanning electron microscopy-energy dispersive X-ray analysis spectrometry (SEM-EDX) has also been used.

X-ray diffraction and i.r. spectroscopy methods measure the bulk composition of a multi-particle dust sample; SEM-EDX measures the elemental composition of single particles. These methods as typically applied, do not distinguish homogeneous distribution of impurities in a particle from possible heterogeneous surface distribution. These measurements of quartz content are not always accurate predictors of the prevalence of dust-induced disease, which implies that the biologically available quartz surface may not be equivalent to conventionally measured quartz content of respirable dust in some exposure settings.

Auger spectrometry and X-ray photoelectron spectrometry can be used to analyze the elemental composition of material surfaces, for surface layer thicknesses from one atomic layer to about 0.001 to 0.01 micrometers deep. However, to distinguish the surface from the underlying material, the surface, after analysis, must be destructively ion-etched off and the underlying material then analyzed. This often requires a number of analyze-and-etch steps. Also, incidental contamination, e.g., carbon from handling or solvents, can mask the surface of interest, requiring careful handling or pre-etching to bare the true surface for analysis.

These problems are exacerbated if one is attempting to study specific components of mixed materials, e.g., quartz respirable-sized particles from a mixed dust atmosphere. In that case, it may be impossible to pre-identify particles of a selected type for detailed surface analysis.

The present invention provides the ability to nondestructively analyze composition with depth below the surface, permitting selection of particles or areas which are then subjected to detailed surface analysis. The method permits identification of differences in the elemental ratios which can distinguish homogeneous composition, top surface coating, and top and bottom surface coating for particles of total thickness between about 0.1 to 10 micrometers.

DISCLOSURE OF THE INVENTION

It is one object of the present invention to provide a differential surface compositional analysis method.

Another object of the present invention is to provide a method for identifying the surface vs. bulk composition of particles.

A further object of the present invention is to provide a method for identifying the composition of particle surfaces which will withstand surface active processes in the lung(s).

A still further object of the present invention is to provide a method for identifying respirable particles which may be pathogenic in the lung.

According to these and other objects of the present invention which will become apparent as the description thereof is presented below, the present invention provides a method of differential surface compositional analysis which involves:

subjecting a solid material to electron beam-induced X-ray spectroscopic analysis with the electron beam accelerated to a first kinetic energy sufficient to analyze material at a first depth below the surface of the solid material without causing surface damage to the solid material;

measuring elemental X-ray signals caused by the electron beam-induced X-ray spectroscopic analysis with the electron beam accelerated to said first kinetic energy;

comparing the measured elemental X-ray signals caused by the electron beam-induced X-ray spectroscopic analysis with the electron beam accelerated to said first and second kinetic energies to determine the differential surface composition of the solid material.

The present invention further provides a method of analyzing the composition of solid particles which involves:

subjecting a solid particle to electron beam-induced X-ray spectroscopic analysis with the electron beam accelerated to a first kinetic energy sufficient to analyze material at a first depth below the surface of the solid particle without causing surface damage to the solid particle;

measuring elemental X-ray signals caused by the electron beam-induced X-ray spectroscopic analysis with the electron beam accelerated to said first kinetic energy;

subjecting the solid particle to electron beam-induced X-ray spectroscopic analysis with the electron beam accelerated to a second kinetic energy sufficient to analyze material at a second depth below the surface of the solid particle without causing surface damage to the solid particle;

measuring elemental X-ray signals caused by the electron beam-induced X-ray spectroscopic analysis with the electron beam accelerated to said second kinetic energy; and comparing the measured elemental X-ray signals caused by the electron beam-induced X-ray spectroscopic analysis with the electron beam accelerated to said first and second kinetic energies to determine the differential surface composition of the solid particle.

Also provided for by the present invention is a method of identifying respirable particles which may be pathogenic in a lung, which method involves:

incubating respirable particles in a surrogate pulmonary surfactant; and subjecting the particles to differential surface compositional analysis to determine the surface composition of the particles before and after incubation.

BRIEF DESCRIPTION OF DRAWINGS

The present invention will be described below with reference to the attached drawings which are given by way of non-limiting examples only, in which:

FIGS. 2(a)-2(l) are plots of the silicon fractions of SEM-EDX signals vs. electron beam accelerating voltage for high silicon composition particles from a clay mine and mill.

BEST MODE FOR CARRYING OUT THE INVENTION

Figure 1:
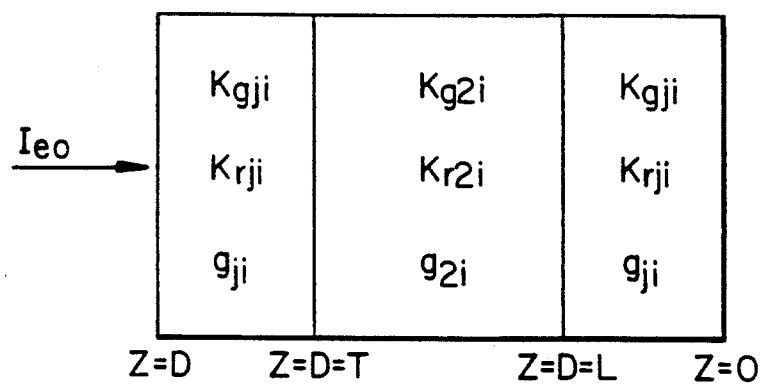
FIG. 1 is a one-dimensional model of a particle of material depicting the co-ordinate system used in the modeling.

The present invention involves subjecting samples of respirable dust to agitated incubation in a surrogate pulmonary surfactant, modelling the hypophase coating of the lung alveoli and respiratory bronchioles, and then microscopically identifying the silica particle fraction of the respirable particles. After identifying the silica particle fraction, surface analysis on the silica particles is performed by one or more methods to determine if they are coated with any mineral material(s) which survives pulmonary surfactant treatment.

According to the present invention, an aqueous dispersion of surfactant is made by ultrasonically mixing dipalmitoyl glycerophosphorylcholine (lecithin) and/or other components of pulmonary surfactant into physiological concentration saline at 37° C. More detailed instructions for suitable surfactant preparation may be found in the Journal of Toxicology and Environmental Health 16: 415-424 (1985), by Wallace et al, the disclosure of which is herein expressly incorporated by reference.

Once the dispersion is prepared, approximately equal amounts of the surfactant and dust, e.g., 1 mg lecithin/ ml physiological saline, 1 mg of dust, is mixed by a suitable method such as vortexing the mixture. Thereafter, the mixture is incubated at 37° C. for about 3 hours, while the mixture is continuously agitated. For purposes of agitating the mixture during incubation, a rotary incubator has been found to be particularly useful for purposes of the present invention.

The incubation time is chosen to represent an estimate of time of incubation of the particle in the pulmonary alveolar hypophase before phagocytosis. Accordingly, the incubation time should be between about 2 to 5 hours and preferably about 3 hours.

Following incubation, a set of quartz particles or other toxic particles of interest are identified by conventional SEM-XRS or optical microscopy. Surface analysis is then performed on the set of particles as discussed in detail below.

Following incubation in the surfactant, an alternative surface analysis protocol was initially used to locate the set of particles of interest on a marked grid by SEM-XRS or optical microscopy. The particles were then re-located and surface analyzed utilizing a scanning Auger spectrometer. This multi-spectrometer approach was later determined to be less functional than the preferred multiple-voltage SEM-XRS analysis method discussed below, because of the need to re-locate particles of interest and because of the potential need to ion-etch residual salts or organics left on the particle surfaces by the surfactant incubation before Auger spectroscopy or photoelectron spectroscopy can detect the mineral surface.

Either of the surface analysis methods may be applied to a statistically significant number of particles which are first identified by conventional microscopy or SEM-XRS to be representative of those considered etiologic agents for pulmonary disease, e.g., high silica (90% or greater Si by SEM-XRS) particles are identified as representative of those responsible for the conventionally measured quartz content of the dust. Comparison of the surface and total composition of a particle then indicates if its biologic activity is masked by a coating insoluble and non-dispersable in pulmonary fluids. The ratio of bare to coated particles of the set then provides a measure of the biologically available fraction of those toxic particles which can be active following deposition in the lung.

Accordingly to a preferred embodiment, the present invention utilizes a minor modification of conventional scanning electron microscopy-energy dispersive X-ray analysis (SEM-EDX) protocols on samples of settled and airborne dust from a clay mine and mill to detect heterogeneity with depth for aluminum impurity in high silica content particles. Utilizing the present invention it is possible to determine whether some of the quartz or "free silica" respirable particles of the dust are occluded with materials such as aluminosilicate.

According to the present invention, electron beam excited X-ray analysis is performed at two or more electron beam accelerating voltages in such a way that near-surface elemental composition of the specimen can be distinguished from the underlying bulk elemental composition. Scanning electron microscopy X-Ray spectrometry (SEM-XRS) can be used to apply the method by operating the system at two or more electron beam accelerating voltages between 20 and 5 kilovolts in the manner described below.

The analysis method described hereafter for determining surface composition may be utilized on elements having atomic numbers as high as calcium. Utilizing SEM-wavelength dispersive X-ray spectrometry and L-line rather than K-line spectra, the method can be utilized to analyze heavier elements.

As will be appreciated, the analysis procedure utilized according to the present invention can be utilized in connection with industrial hygiene respirable particle analysis, mineralogical analysis, metallurgy and ceramics analysis for fouling, slagging, corrosion, and other material processes, petroleum and chemical engineering for catalyst surface studies, and other applications.

According to the surface analysis method of present invention, a solid material whose elemental composition is to be analyzed for possible heterogeneity with depth below the surface is subjected to electron beam-induced X-ray spectroscopic analysis with the electron beam accelerate to a kinetic energy of above 10 kilo-electron volts (keV) or more. The energy is picked to be high enough to analyze a selected depth and low enough to avoid surface damage. The ratios of the elemental X-ray signals are measured. Then the electron beam energy is reduced in one or two steps. This can be done using conventional scanning electron microscope X-ray spectrometers or electron microprobe analyzers, which are operated at two or more electron beam accelerating voltages between about 20 and 5 keV.

As the beam voltage is reduced, the electrons excite X-rays to at lesser depths. The limitation is that the electron energy must be greater than the photon energy of the elemental line to be excited. The effect of proximity of the excitation energy and X-ray energy is accounted for to first order in the analysis part of the present method; however, it is recommended to use electron energies of at least twice the energy of the X-ray to be excited. For K-shell X-ray lines this means electrons with energies as low as 4 to 5 keV can be used to analyze silicon and lower atomic number elements. For heavy elements, above calcium, the L-line of higher line spectra rather than the K-line spectra permit using beams of electron energy down to 3 to 5 volts for near surface analysis.

By using two excitation voltages sequentially, such as 20 and 5 keV, the ratios of elemental line strengths can be ratioed at each voltage and then the ratios between the two voltages compared between the two voltages to determined if there is heterogenicity of elemental composition with depth into the material. By using several voltages a map of composition with depth can be determined for thicknesses starting about 0.01 to 0.1 micrometer of material nearest the surface down to about 1 to 10 micrometers thickness, depending on the material being analyzed.

To account for changes in the ratios due to changing differences between the excitation energies and the energies of the X-ray lines being excited, to account for material densities, and to distinguish the effects of coatings on the top, or both sides of a material, the ratios of the elemental line strengths were measured versus excitation voltage, and these data were compared with mathematical model formula prediction of ratio versus voltage for homogeneous structure and for the two heterogeneous structure models of top, and top and bottom coating. An analytic model was than developed, as discussed below.

Utilizing SEM-EDX analysis an incident electron beam penetrates a sample and loses energy in inelastic collisions, some of which excite X-ray emissions characteristic of the elements present. Within any layer at a given depth in the particle the intensity of an X-ray line stimulated by inelastic electron collision with a specific element is proportional to: (a) the concentration of target atoms; (b) the intensity, in terms of electrons with energy sufficient to stimulate emission of the characteristic X-rays, of the electron beam in the layer; (c) the cross-section for ionization of the target atom shell by those electrons; and (d) the fluorescence yield, which is the probability that the ionization will result in that X-ray emission.

In the following example, calculation and experimental analysis, silica quartz particles are analyzed for aluminosilicate clay surface coatings. Thus, values for silica and aluminum are used in the equation parameters. Analysis for other particle and coating combinations would use parametric values appropriate for the elements considered.

A clay-occluded quartz particle of thickness D can be taken to be represented as aluminosilicate coatings of equal atomic percentage Si and Al on the top and bottom faces of a pure silica layer. The top coating is of thickness T, the bottom coating is of thickness D-L, and the silica interior is of thickness L-T. For mathematical convenience the co-ordinate z was measured from the bottom of the particle, as shown in FIG. 1, which depicts a one-dimensional model of a particle designated j=2, coated on the top and bottom with material designated j=1. Distances are measured from the bottom of the particle at z=0. An electron beam of intensity $I_{eo}$ is incident on the top of the particle at z=D. In FIG. 1, terms designating electron beam intensity extinction coefficients, $K_{eji}$, X-ray generation coefficients, $g_{ji}$, and X-ray extinction coefficients, $k_{rji}$, are shown for each layer.

An electron beam of intensity $I_{eo}$ incident on the top at z=D was taken to be monochromatic with energy $V_o$keV. The beam intensity is attenuated and a distribution of lower electron kinetic energies produced as the electrons penetrate the particle. The intensity of the beam in material j at level z with sufficient energy to excite X-rays of frequency i is $I_{eji}(z)$. Here j=1 designates the top or bottom aluminosilicate coating and j=2 designates the silica core. Diminution of electron beam intensity with depth into a particle was modelled as a one-dimensional Beer's law process with extinction coefficeint $k_{eji}$; $dI_{eji}(z)=k_{eji}I_{eji}(z)dz$. This was used as the basis for a simple one-dimensional mathematical model with analytical solutions for the silicon fraction of signal vs electron beam accelerating voltage by setting $k_{eji}=3/R_{ji}$, where $R_{ji}$ is the depth in $\mu$m in material j to which an incident electron of energy $V_o$keV can excite an X-ray emission of characteristic energy $V_i$keV. This depth was taken to be: $R_{ji}=0.064\text{-}(V_o^{1.68}-V^{1.68})/p_j$, where $p_j$ is the density of material j in g ml$^{-1}$.

Integrating the Beer,s law differential equations for $I_{eji}$ through the particle depth with boundary conditions of continuous values of intensity across the two material interfaces at z=D−T and z=D−L, resulted in electron beam intensities in each of three material layers, from top to bottom, of:

$$I_{e1i}(Z)=I_{eo}e^{-ke1i(D-Z)} \quad (1)$$

$$I_{e2i}(Z)=I_{eo}e^{-(ke1i-ke2i)T_e-ke2i(D-z)} \quad (2)$$

$$I_{e1i}(Z)=I_{eo}e^{-(ke1i-ke2i)T_e-(ke2i-ke1i)L_e-ke1i(D-Z)} \quad (3)$$

Intensity of X-rays of frequency i travelling in the positive z-direction in material j at level z is designated $I_{rji}(z)$ Inelastic collisions of electrons with atoms of specific elements in a thin layer dz in material j at level z generates X-rays of intensity $dI_{rji}(z) = g_{ji}w_j I_{eji}(z)dz$, where $g_{ji}$ relates electron beam intensity and ionization of inner shell electrons which can result in X-rays of frequency i, and $w_j$ is the probability that the ionization will result in X-ray rather than Auger electron emission.

The ionization coefficient $g_{ji}$ is a function of the energy of an electron colliding with an atom and the energy required to induce the specific ionization. This would require an expression for the distribution of electron energies as a function of depth into the particle in order to calculate absolute values of X-ray line intensities induced throughout a particle. In order to limit the present analyses to ratios of X-ray line intensities for different elements induced by different electron beam voltages, a simple empirical proportionality between X-ray intensity and $V_o$ alone: $g_{ji} = P_j(V_o - V_j)^{1.65}$, was used where $P_j$ is the atomic fraction of silicon to silicon plus aluminum in material j. Tabulated values of $V_j$ and $w_j$ are available for the elements of interest here.

Secondary X-ray fluorescence, not included in this model, would result in the generation of some additional aluminum X-rays throughout a particle. Attenuation of emerging characteristic X-rays i by a thin layer of material j is also modelled by a Beer's law diminution with X-ray extinction coefficient $k_{rji}$, which is the mass composition-weighted sum of the extinction coefficients of each element in the material. These expressions for the extinction of electron beam intensity and the consequent generation and extinction of X-rays across a small thickness dz of material provide a system of differential equations which describe the change in intensity of X-rays in each of the three material layers, from top to bottom, of a particle:

$$dI_{r1i}(Z) = -k_{r1i}I_{r1i}(z)dz + g_{1i}w_i I_{eo} e^{-k_{e1i}(D-z)}dz \text{ for } D > z > D-T, \quad (4)$$

$$dI_{r2i}(z) = -k_{r2i}I_{r2i}(z)dz + g_{2i}w_i I_{eo} e^{-(k_{e1i}-k_{e2i})T} e^{-k_{e2i}(D-z)}dz \text{ for } D-T > z > D-L, \quad (5)$$

$$dI_{r1i}(z) = -k_{r1i}I_{r1i}(z)dz + g_{1i}w_i I_{eo} e^{-(k_{e1i}-k_{e2i})T} e^{-(k_{e2i}-k_{e1i})L} e^{-k_{e1i}(D-z)}dz \text{ for } D-L > z > 0. \quad (6)$$

These differential equations were integrated subject to the boundary conditions that X-ray flux is continuous across the two material interfaces: $I_{r1i}(D-T) = I_{r2i}(D-T)$, and $I_{r2i}(D-L) = I_{r1i}(D-L)$. The intensity of X-rays of frequency i emitted from the top of the particle is $$I_{r1i}(z = D) = \frac{g_{1i}w_i I_{eo}}{k_{r1i} + k_{e1i}} [1 - e^{-(k_{e1i}+k_{r1i})T}] + \frac{g_{2i}w_i I_{eo}}{k_{r2i} + k_{e2i}} e^{-(k_{e1i}-k_{e2i})T} e^{-k_{e2i}L} e^{-k_{r1i}T} [e^{k_{e2i}(L-T)} - e^{-k_{r2i}(L-T)}] + \frac{g_{1i}w_i I_{eo}}{k_{r1i} + k_{e1i}} e^{-(k_{e1i}-k_{e2i})T} e^{-(k_{e2i}-k_{e1i})L} e^{-k_{e1i}D} e^{-k_{r2i}(L-T)} e^{-k_{r1i}T} [e^{k_{e1i}(D-L)} - e^{-k_{r1i}(D-L)}].$$

where the three sets of terms represent contributions to the X-ray intensity by the top to bottom layers of the particle, respectively. The fractional silicon signal as a function of incident electron energy is predicted by using this expression in : $f_{si} = I_{r1Si}(D)/(I_{r1Si}(D) + I_{r1Al}(D))$.

For comparison with experimental data for measured $f_{si}$ vs $V_o$, it was assumed that there was an equal thickness of top and bottom layers of clay on a silica core. Then the expressions for emitted X-ray intensities used to calculate $f_{si}$ were:

$$I_{r1i}(z = D) = \frac{g_{1i}w_i I_{eo}}{k_{r1i} + k_{e1i}} [1 - e^{-(k_{e1i}+k_{r1i})T}] + \quad (8)$$

$$\frac{g_{2i}w_i I_{eo}}{k_{r2i} + k_{e2i}} e^{-k_{e2i}(D-T)} e^{-k_{r1i}T} [e^{k_{e2i}(D-2T)} - e^{-k_{r2i}(D-2T)}] +$$

$$\frac{g_{1i}w_i I_{eo}}{k_{r1i} + k_{e1i}} e^{-k_{e1i}D} e^{-k_{r2i}(D-2T)} e^{k_{r1i}T} [e^{k_{e1i}T} - e^{-k_{r1i}T}].$$

The mass composition-weighted X-ray extinction coefficients for this clay-occluded quartz model, in units of $\mu m^{-1}$, are: $k_{r1Si} = 0.3642$, $k_{r1Ai} = 0.2653$, $k_{r2Si} = 0.1820$, $k_{r2Ai} = 0.2818$. The X-ray generation coefficients used were $g_{1Ai} = 0.5(V_o - 1.487)_{1.65}$, $g_{2Ai} = 0$, $g_{1Si} = 0.5(V_o - 1.740)^{1.65}$, $g_{2Si} = (V_o - 1.740)^{1.65}$. The coefficients for electron beam extinction were $k_{e1Ai} = k_{e2Ai} = 117.2(V_o^{1.68} - 1.487^{1.68})^{-1}$, and $k_{e1Si} = k_{e2Si} = 117.2(V_o^{1.68} - 1.740^{1.68})^{-1}$.

The expression for emission of X-rays of frequency i from a silica particle of thickness D, but with a homogeneous distribution of aluminum throughout, similarly derived using the same assumptions and modelling procedure, is:

$$I_{ri}(z = D) = \frac{g_i w_i I_{eo}}{k_{ri} + k_{ei}} [1 - e^{-(k_{ei}+k_{ri})D}]. \quad (9)$$

For a homogeneous particle of thickness D and specific gravity 2.5, with composition $Si_p O_{2p} Al_{(1-p)} O_{1.5(1-p)}$, where p is the atomic fraction of silicon to silicon plus aluminum, the value for the X-ray attenuation coefficients are $k_{rSi} = 1.5 (1118080 + 74400 \text{ P}) / (51 + 9 \text{ P})$, and $k_{rAi} = 2.5(50109 + 17507P)/(51 + 9P)$. The electron beam diminution coefficients are the same as in the heterogeneous model, and the X-ray generation coefficients are $g_{Si} = P(V_o - 1.740)^{1.65}$, and $g_{Ai} = (1-P)(V_o - 1.487)^{1.65}$.

The following examples are presented to illustrate features and characteristics of the present invention which is not intended to be considered as being limited thereto.

EXAMPLE 1

In this example, dust particles with suspected heterogeneous surfaces were analyzed to determine material composition with depth to the particle. Accordingly, settled dust and airborne dust samples were collected from a clay mine and mill which had been selected as one in which some significant "free silica" quartz dust fraction might be found together with individual quartz particles having some associated aluminosilicate impurity.

Samples of collected dust were analyzed first for quartz content by Fourier transform i.r. spectroscopy (Nicolet Model 20SXC FTIR), using the i.r. spectral peak height of silica at 795 cm$^{-1}$, corrected by subtracting the aluminosilicate peak height at 910 cm$^{-1}$, for sample of 30–300 $\mu$g. Sample preparation and calibration curve protocols were used to monitor the "free silica" content of U.S. mine dusts. Samples found to be between 7 and 12% quartz by mass were selected for analysis by SEM-EDX.

For a number of those individual particles SEM-EDX (ETEC Autoscan SEM, Serial No. 33; EG&G Ortec Model EDDS-II signal processor), with the $K\alpha$ lines excited by electron beam, was used to analyze for aluminum and silicon. The working distance from objective lens to sample was 27 mm. The electron beam diameter was nominally 0.015 $\mu$m. Dusts were mounted on carbon support stubs and were carbon coated under vacuum using a Polaron E6100 coater. ECX analysis of particle-free regions of the stub showed no silicon or aluminum above the Bremsstrahlung background. Particle imaging was by secondary electron detection.

Particles analyzed were less than 3 $\mu$m in width; thus for particles of the density of aluminosilicate they were well within the respirable size range. Particles were individually analyzed for elemental composition by SEM-EDX using an electron beam accelerating potential of 20 keV. Spectra were accumulated for 60 s. Particles whose spectra at 20 keV excitation had a silicon fraction of signal, $f_{Si}=I_{Si}/(I_{Si}+I_{Ai})$, of 0.9 or greater were considered to be the particles responsible for the quartz content of the dust as measured by i.r. spectroscopy.

These "high-silica" particles were then subjected to SEM-EDX analysis at a series of electron beam accelerating voltages from 20 down to 5 keV. The attempt was made to hold the electron beam at one spot on the particle being analyzed, while up to 10 sets of data were taken at each voltage. Each set represented EDX signal acquisition for 60 s. Several high-silica particles were imaged at two sample stage angles 45° apart to determine that they were not plate-like in shape. Subsequently, measurements of particle width were made from photographs of the SEM images; these widths were used as approximations for particle thickness in the data analysis.

Most particles from the clay mine and mill dusts had a silicon fraction $f_{Si}$, derived from SEM-EDX measurements, of about 0.5 for 20 keV applied voltage; that is, most appeared to be aluminosilicate clay particles. Elemental spectral lines other than those of silicon or aluminum accounted for 1% or less of the observed signals. Particle by particle visual search was used to identify a number of particles for which the silicon fraction of signal at 20 keV was 0.9 or greater. These "high-silica" particles were assumed to be representative of the particles which are the source of the measured "free-silica" content of the dust samples.

Some 40 such high silica particles were identified and further analyzed for silicon fraction of signal at incident electron energies between 20 and 5 keV. The particles did not appear in their images to be agglomerates. The approximate widths of these particles ranged from 0.5 to 3 $\mu$m. At lower incident electron beam accelerating voltages all but three of the high silicon particles surveyed showed a decrease in the silicon fraction of signal down to values equal to or less than 0.8 at 5 keV. The intention here was not to perform a statistical survey of dust composition, but to try to locate some high silicon spectra particles with low but non-zero aluminum signal, for SEM-EDX analysis at several electron beam voltages. Results for four typical high-silica particles are shown in FIGS. 2(a)-(d) and 3.

FIGS. 2(a)-(d) show the silicon fraction of signal measured at five different electron beam accelerating voltages, 5, 7, 9, 11 and 20 keV, for each of four high-silica particles. The following parameters are illustrated in the indicated FIGS. 2(a)-2(d): 2(a) particle of approximately 0.8 $\mu$m width with silicon fraction of signal, $I_{Si}/(I_{Si}+I_{aj})$, at 20 keV of 0.9358; 2(b) particle of approximately 1.0 $\mu$m width with silicon fraction of signal at 20 keV of 0.9411; 2(c) particle of approximately 2.0 $\mu$m width with silicon fraction of signal at 20 keV of 0.9407; 2(d) particle of approximately 1.5 $\mu$m width with silicon fraction of signal at 20 keV of 0.9543. The mean and standard deviation of 10 measurements of 60 s signal accumulation time per measurement for each of the five acceleration voltages are shown by error flags in FIGS. 2(a)-(d) for each particle. The solid line segments connect the mean values of the experimental data points. The dashed lines show behavior predicted by a model of silica particles homogeneously contaminated with alumina, as discussed above; the dotted lines show behavior predicted by a model of silica particle cores with aluminosilicate coatings, as also discussed above.

SEM-EDX spectra were taken at voltages of 5, 7, 9, 11 and 20 keV on each of four high-silica particles after incubation in dipalmitoyl lecithin surfactant followed by rinsing with distilled water. For all four of these particles the silica fraction of signal fell with decreasing electron accelerating voltage, to values below 0.8 at 5 keV, behavior which was similar to that of other high silica particles in FIG. 2.

Data for four particles which were high in concentration of silica and come from the clay mine and mill are shown in FIGS. 2(a)-(d) and are consistent with the predictions of the heterogeneous particle surface composition model plotted in the figures as dotted lines. The dashed lines show the predictions of the homogeneous model. To calculate the predictions $f_{Si}$ measured at 20 keV was used as an approximation for the true value for the whole particle. The observed width of the particle was taken to be its thickness, which is an acceptable approximation for silica but can be seriously in error for clays, which tend to flake, resulting in plate-like particles.

EXAMPLE 2

In this example SEM-EDX analysis at five voltages for silicon fraction of signal was performed on a sample of albite, an aluminosilicate mineral with Si-Al atomic ratios of about 3:1. This sample is used to provide homogeneous particles; that is, particles with the same surface and bulk composition which serve as a control to show the results of the analysis on a particles with no heterogeneous coating. Ten measurements of $I_{Si}/(I_{Si}+I_{Ai})$ at each of five voltages were made on each of four albite particles, each particle being approximately 1 $\mu$m in diameter.

Figure 3:
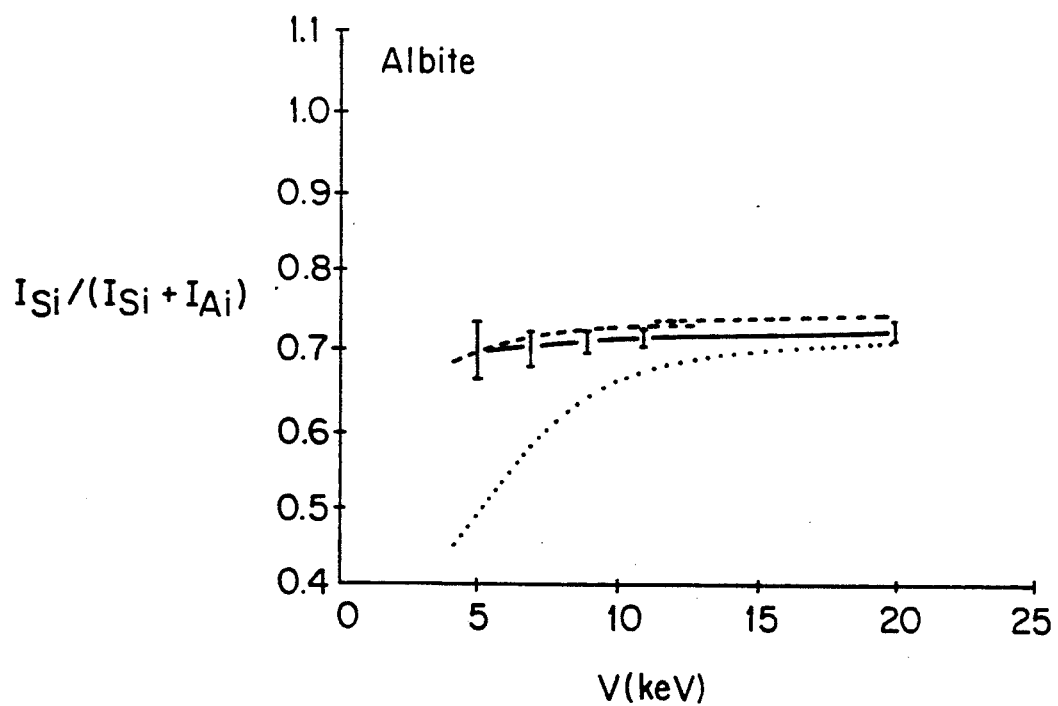
FIG. 3 is a plot of the silicon fractions of SEM-EDX signals vs. electron beam accelerating voltage for albite particles.
Figure 2A:
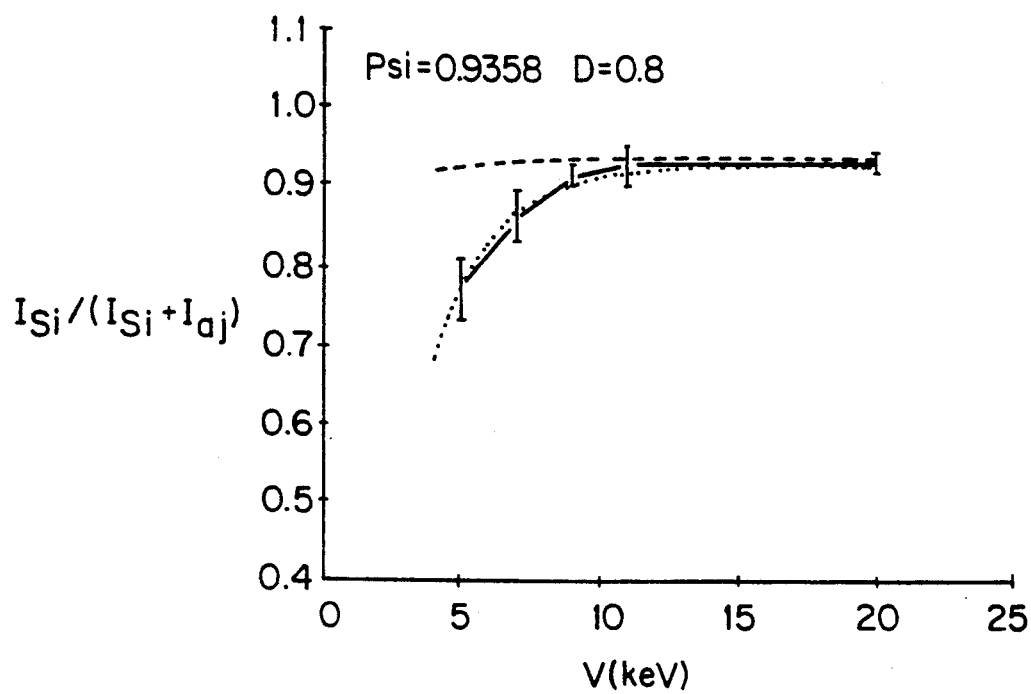
Figure 2B:
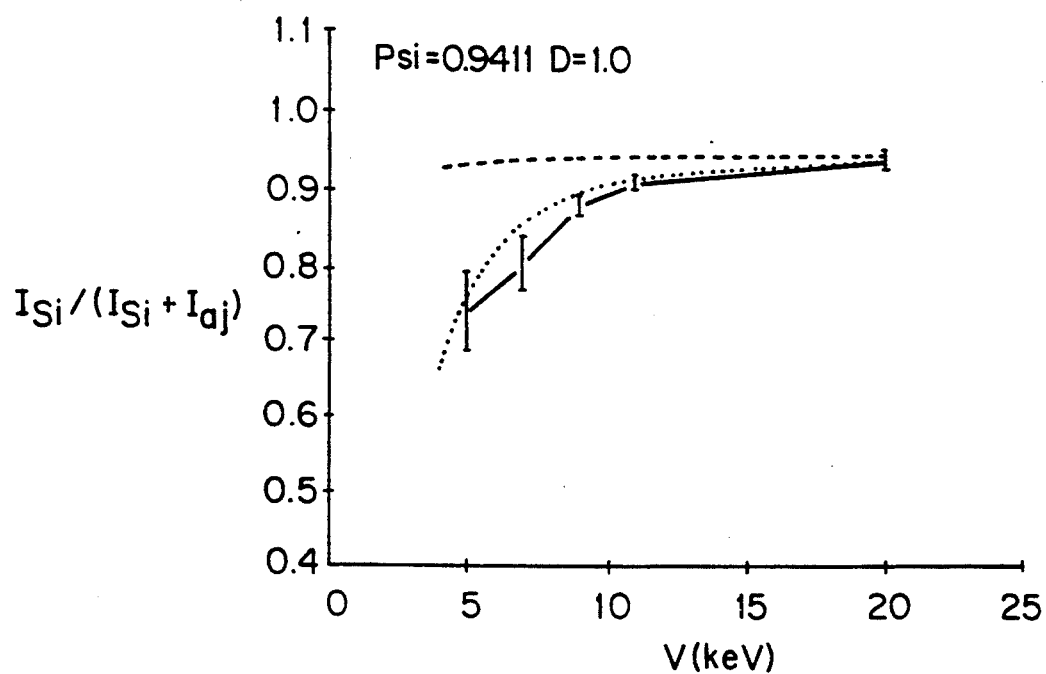
Figure 2C:
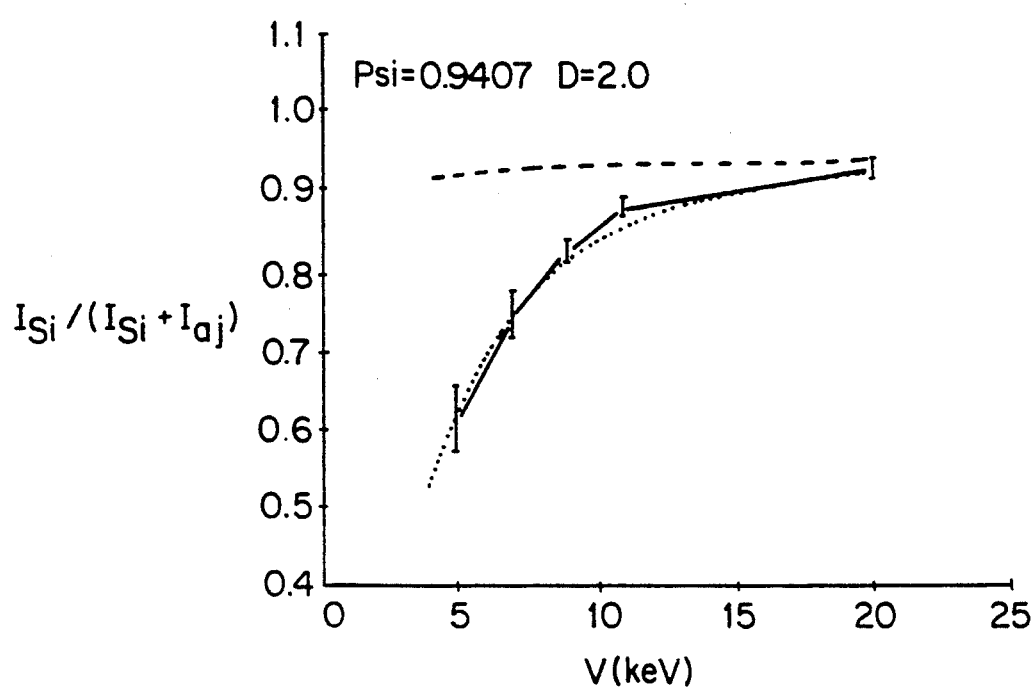
Figure 2D:
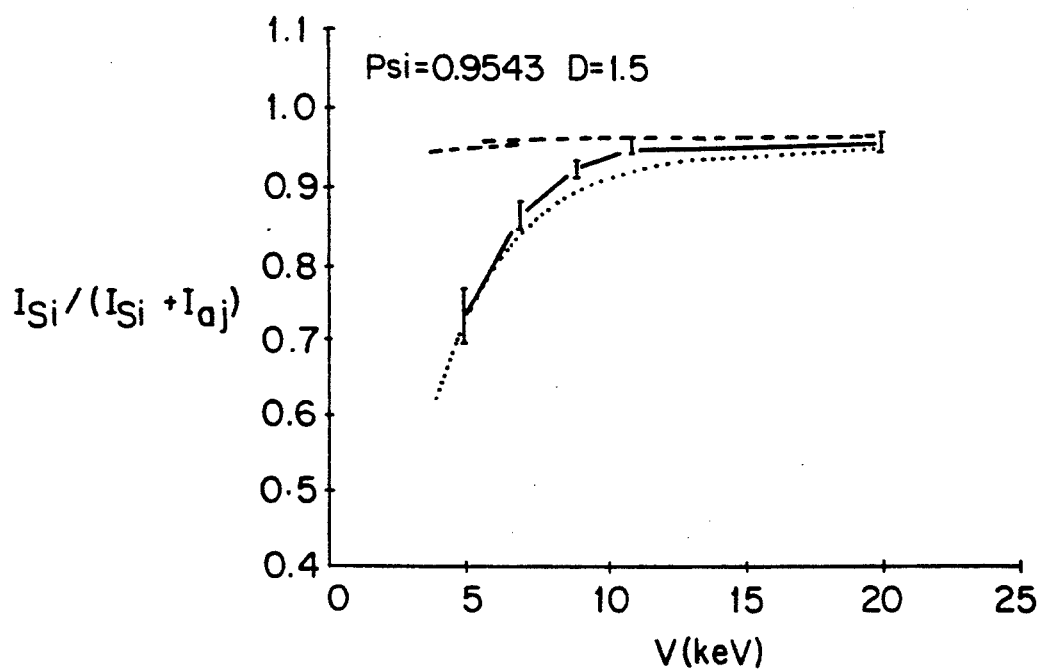

FIG. 3 shows the behavior of silicon fraction of signal versus electron beam accelerating voltage for particles of the mineral albite, a homogeneous aluminosilicate. The experimental data in FIG. 3 show the combined data for 10 measurements of $I_{Si}/(I_{Si}+I_{Ai})$ at each of five voltages made on each of four particles of approximately 1 $\mu$m dia: thus standard deviations are shown for 40 measurements of the silicon fraction of signal at each voltage. The FIG. 3 also shows the silicon fraction of signal versus electron accelerating voltage predictions of the homogeneous and heterogeneous composition models discussed below. As FIG. 3 shows, the homogeneous particles follow the model for homogeneous particle structures.

When the concentration of aluminum impurity exceeds about 1% it was possible to distinguish heterogeneous from homogeneous particles using the system and signal averaging times used here. Each particle had 10 measurements of $f_{Si}$ taken at each of five voltages, each measurement accumulating X-ray spectra for 60 s. Since the method involves use of incident electron energies down to 5 keV the elemental X-ray lines must be of energy less than 2 keV, so that if K radiation is used the method is restricted to Na, Si, Al and Mg. The use of wavelength dispersive spectrometry to detect L-series lines might alleviate this restriction.

EXAMPLE 3

To simulate particle residence in the hypophase fluid which coats the surface of the respiratory bronchioles and pulmonary alveoli in the deep lung air spaces and to determine the effects of this incubation on surface coatings on these particles, one sample of the mine and mill clay dust from example 1 above was mixed into a dispersion of dipalmitoyl glycerophosphorylcholine (lecithin), (mass concentration 1 mg dust per ml lecithin dispersion), in a rotary incubator for 3 hours at 37° C. The lecithin dispersion of 1 mg lecithin per ml physiological concentration saline was made by sonication at 40 W for 10 min. After incubation the dust was centrifuged at 2000 g, the supernatant discarded, and the dust was rinsed thrice by resuspension in distilled water and re-centrifugation. An aliquot of the final suspension was dried on a carbon SEM stub. Four high-silica particles were identified by SEM-EDX at 20 keV, and subsequently spectra at the four lower voltages down to 5 keV were taken for silicon and aluminum for each of the four particles.

Subsequent depth profiling at low voltages showed behavior similar to that in FIG. 2; that is, particles had retained clay occlusion on their surface. Viewed by secondary electron SEM these high-silica particles did not appear to be agglomerates, which suggest that after deposition in the lung, and before phagocytosis by pulmonary macrophages, some quartz particles would present themselves as clay-surfaced.

The longer-term fate of such coatings during phagolysosomal events and clearance or sequestration in the lung would determine if and when the quartz content of the particle becomes biologically available to tissue. Conventional i.r. spectroscopic and X-ray diffraction methods applied to these samples would therefore appear to provide quartz content measurements which do not necessarily reflect the amount of biologically available quartz.

Although the invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A method of differential surface compositional analysis which comprises:
    subjecting a solid material to electron beam-induced X-ray spectroscopic analysis with the electron beam accelerated to a first kinetic energy sufficient to analyze material at a first depth below the surface of said solid material without causing surface damage to said solid material;
    measuring elemental X-ray signals caused by said electron beam-induced X-ray spectroscopic analysis with the electron beam accelerated to said first kinetic energy;
    subjecting said solid material to electron beam-induced X-ray spectroscopic analysis with the electron beam accelerated to a second kinetic energy sufficient to analyze material at a second depth below the surface of said solid material without causing surface damage to said solid material;
    measuring elemental X-ray signals caused by said electron beam-induced X-ray spectroscopic analysis with the electron beam accelerated to said second kinetic energy; and
    comparing said measured elemental X-ray signals caused by said electron beam-induced X-ray spectroscopic analysis with the electron beam accelerated to said first and second kinetic energies to determine the differential surface composition of said solid material.

2. A method of differential surface compositional analysis according to claim 1, wherein said first and second kinetic energies are between about 5 and 20 keV.

3. A method of differential surface compositional analysis according to claim 1, wherein said comparing comprises determining the ratios of the elemental X-ray signals caused by said electron beam-induced X-ray spectroscopic analysis with the electron beam accelerated to a first and second kinetic energies and comparing the ratios to determine composition of said solid material with respect to surface depth.

4. A method of differential surface compositional analysis according to claim 1, wherein said elemental X-ray signals comprise K-line spectra signals.

5. A method of differential surface compositional analysis according to claim 4, wherein said first and second kinetic energies are between about 4 and 20 keV.

6. A method of differential surface compositional analysis according to claim 1, wherein said elemental X-ray signals comprise L-line spectra signals.

7. A method of differential surface compositional analysis according to claim 6, wherein said first and second kinetic energies are between about 3 and 20 keV.

8. A method of differential surface compositional analysis according to claim 1, wherein said surface of said solid material is analyzed to a depth of about between 0.1 to 10 microns.

9. A method of analyzing the composition of solid particles which comprises:
    subjecting a solid particle to electron beam-induced X-ray spectroscopic analysis with the electron beam accelerated to a first kinetic energy sufficient to analyze material at a first depth below the surface of said solid particle without causing surface damage to said solid particle;
    measuring elemental X-ray signals caused by said electron beam-induced X-ray spectroscopic analysis with the electron beam accelerated to said first kinetic energy;
    subjecting said solid particle to electron beam-induced X-ray spectroscopic analysis with the electron beam accelerated to a second kinetic energy sufficient to analyze material at a second depth below the surface of said solid particle without causing surface damage to said solid particle;

measuring elemental X-ray signals caused by said electron beam-induced X-ray spectroscopic analysis with the electron beam accelerated to said second kinetic energy; and comparing said measured elemental X-ray signals caused by said electron beam-induced X-ray spectroscopic analysis with the electron beam accelerated to said first and second kinetic energies to determine the differential surface composition of said solid particle.

10. A method of analyzing the composition of solid particles according to claim 9, wherein said solid particles comprise respirable dust particles.

11. A method of analyzing the composition of solid particles according to claim 9, wherein the solid particles are initially analyzed by infrared spectroscopy to determine mass elemental percentages.

12. A method of analyzing the composition of solid particles according to claim 11, wherein said solid particles are initially analyzed for silica content.

13. A method of identifying respirable particles which may be pathogenic in a lung, which method comprises:

incubating respirable particles in a surrogate pulmonary surfactant; and subjecting said particles to differential surface compositional analysis to determine the surface composition of said particles, wherein said differential surface compositional analysis comprises:

subjecting respirable particles to electron beam-induced X-ray spectroscopic analysis with the electron beam accelerated to a first kinetic energy sufficient to analyze material at a first depth below the surface of said solid particle without causing surface damage to said solid particle;

measuring elemental X-ray signals caused by said electron beam-induced X-ray spectroscopic analysis with the electron beam accelerated to said first kinetic energy;

subjecting said solid particle to electron beam-induced X-ray spectroscopic analysis with the electron beam accelerated to a second kinetic energy sufficient to analyze material at a second depth below the surface of said solid particle without causing surface damage to said solid particle;

measuring elemental X-ray signals caused by said electron beam-induced X-ray spectroscopic analysis with the electron beam accelerated to said second kinetic energy; and comparing said measured elemental X-ray signals caused by said electron beam-induced X-ray spectroscopic analysis with the electron beam accelerated to said first and second kinetic energies to determine the differential surface composition of said solid particle.

14. A method of identifying respirable particles according to claim 13, further comprising subjecting said particles to differential surface compositional analysis before and after said incubation to determine changes in surface composition of said particles before and after said incubation.

15. A method of identifying respirable particles according to claim 14, wherein said respirable particles comprise dust particles and said hazardous component comprises silica.

16. A method of identifying respirable particles according to claim 13, wherein said respirable particles comprise dust particles.

17. A method of identifying respirable particles according to claim 13, wherein said surrogate pulmonary surfactant comprises a dispersion of dipalmitoyl glycerophosphorylcholine.

18. A method of identifying respirable particles according to claim 13, wherein said particles are agitated during said incubation.

* * * * *